United States Patent [19]

Afonso

[11] 4,448,782

[45] May 15, 1984

[54] 2-(AMINO ACID-THIO)-2-PENEM-3-CARBOXYLIC ACIDS AND CONGENERS

[75] Inventor: Adriano Afonso, West Caldwell, N.J.

[73] Assignee: Schering Corporation, Kenilworth, N.J.

[21] Appl. No.: 316,702

[22] Filed: Oct. 30, 1981

Related U.S. Application Data

[63] Continuation-in-part of Ser. No. 125,811, Feb. 28, 1980, abandoned.

[30] Foreign Application Priority Data

Feb. 20, 1981 [EP]  European Pat. Off. ......... 81101210.3

[51] Int. Cl.³ .................. C07D 499/04; A61K 31/425
[52] U.S. Cl. ............................. 424/270; 260/245.2 R; 260/239 A
[58] Field of Search ................. 260/245.2 R; 424/270, 424/271

[56] References Cited

U.S. PATENT DOCUMENTS

| | | | |
|---|---|---|---|
| 4,272,437 | 6/1981 | Menard | 260/239.1 |
| 4,290,948 | 9/1981 | Brain et al. | 260/245.2 R |
| 4,301,074 | 11/1981 | Christensen et al. | 260/245.2 R |

FOREIGN PATENT DOCUMENTS

| | | |
|---|---|---|
| 23887 | 8/1979 | European Pat. Off. . |
| 2013674 | 8/1979 | United Kingdom . |

*Primary Examiner*—Nicholas S. Rizzo
*Attorney, Agent, or Firm*—Anita W. Magatti; Gerald S. Rosen

[57] ABSTRACT

6-Substituted-hydrocarbon-2-(amino acid-thio)penem-3-carboxylic acids and congeners having useful antibacterial activity are disclosed. The compounds are prepared in a reaction sequence starting with a 4-acyloxy-2-azetidinone.

13 Claims, No Drawings

2-(AMINO ACID-THIO)-2-PENEM-3-CARBOXYLIC ACIDS AND CONGENERS

This application is a continuation-in-part of my co-pending application U.S. Ser. No. 125,811 filed Feb. 28, 1980 now abandoned.

The present invention relates to 2-(amino acid thio)-2-penem-3-carboxylic acids and congeners. More particularly, this invention relates to compounds of the formula

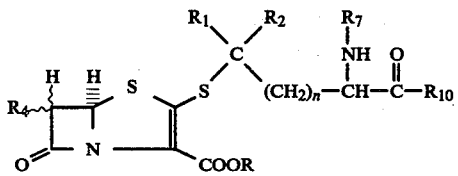

wherein n is 0 to 4;

R is hydrogen, an alkali metal or quaternary ammonium cation or a metabolisable ester group;

$R_1$ and $R_2$ are independently hydrogen or loweralkyl;

$R_4$ is hydrogen, lower alkyl or a group of the formula

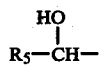

$R_5$ is hydrogen, lower alkyl, aryl, aralkyl, heteroaryl or heteroaralkyl;

$R_{10}$ is amino, lower alkylamino, an α-amino acid residue bonded through the α-nitrogen atom, or $-OR_6$ wherein $R_6$ is hydrogen, lower alkyl, allyl, aryl, aralkyl or quaternary ammonium cation or a metabolisable ester group.

$R_7$ is hydrogen, loweralkyl, aryl, aralkyl, arylsulfonyl, acyl, a 1,3-dicarbonyl adduct, a Schiff's base, an amidine or guanidine group.

The penems of this invention are named by reference to the following formula

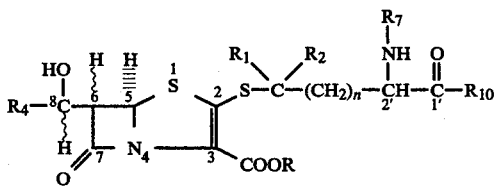

The lower alkyl groups referred to above contain 1 to 6 carbon atoms and are exemplified by methyl, ethyl, propyl, butyl, pentyl, hexyl, and the corresponding branched chain isomers thereof.

The term "acyl" as used herein denotes groups of the formula

wherein $R_8$ is lower alkyl, aralkyl, lower alkoxy, aryloxyl, alkenyl or alkynyl of 2–6 carbon atoms, cycloalkyl of 4–6 carbon atoms, heteroaryl, heteroaralkyl, optionally substituted by hydroxy, thiol, alkylthio, lower alkyl, lower alkoxy, halogen, cyano, carboxy, nitro, amino, aminoloweralkyl or haloloweralkyl such as trifluoromethyl. Representative of such groups are those such as benzyl, p-hydroxybenzyl, 4-amino-4-carboxybutyl, methyl, cyanomethyl, 2-pentenyl, n-amyl, p-heptyl, ethyl, 3- or 4-nitrobenzyl, phenethyl, α,β, -diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl), 5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, p-carboxymethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolylmethyl, 2-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotrizolyl)methyl, difluoromethyl, dichloromethyl, dibromomethyl, 1-(3-methylimidazolyl)methyl, 2- or 3-(4-carboxymethylthienyl)methyl, 2- or 3-(5-methylthienyl)methyl, 2- or 3-(methoxythienyl)methyl, 2- or 3-(4-chlorothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl, cyclohexylamidinomethyl and other similar acyl groups found in conventional penicillin derivatives. The term also denotes an acyl residue derived from an α-amino acid of the L or D configuration.

The term aryl as used herein refers to phenyl substituted by zero to three lower alkyl, lower alkoxy or halogen groups, e.g., p-tolyl, o-tolyl, m-tolyl, p-chlorophenyl, o-methoxyphenyl, 2-methyl-3-fluorophenyl, etc.

The term halogen as used herein refers to fluorine, chlorine, bromine and iodine.

Heteroaralkyl as used herein refers to lower alkyl groups substituted by a heteroaryl group.

As used herein, the term heteroaryl encompasses five- and six-membered heterocyclic groups containing from one to four nitrogen, oxygen or sulfur groups, optionally substituted by lower alkyl groups. Representative heteroaryl groups are those such as pyridyl, furanyl, thienyl, quinolinyl. The term is intended to cover all isomers, e.g., 2-pyridyl, 3-pyridyl and 4-pyridyl.

The lower alkoxy groups referred to above contain 1 to 6 carbon atoms and are exemplified by methoxy, ethoxy, propoxy, butoxy, pentoxy, hexoxy and the corresponding branched chain isomers thereof.

The term aralkyl denotes a lower alkyl group substituted by one or two aryl groups, e.g., benzyl, phenethyl, benzhydryl and the like, which each may be optionally substituted by one to three lower alkyl, lower alkoxy or halogen groups.

The term metabolisable ester group denotes an ester group which is metabolically removed in the body. Two particularly useful metabolisable ester groups are the phthalidyl group and the pivaloyloxymethyl group.

The term 1,3-dicarbonyl adduct as used herein refers to the addition product between the amino group of the amino acid carbon and a 1,3-dicarbonyl compound of the formula

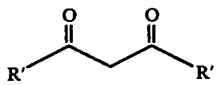

wherein the R' groups can be alike or different and one selected from the group consisting of lower alkyl,-coo lower alkyl or together may be part of a cyclic ring structure. Representative 1,3-dicarbonyl compounds utilized are those such as methyl acetoacetate, dihydroresorcinol, dimedone and acetyl acetone.

The term amidine and guanidine as used herein refers to the derivatized amino group of the amino acid carbon wherein the derivatized amino group has the formula

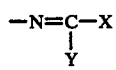

wherein X and Y are as defined in Belgian Patent 848,545, the teachings of which are herein incorporated by reference.

The term Schiff's base as used herein refers to the addition of product between the amino group of the amino acid carbon and an aldehyde or ketone of the formula

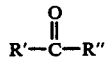

where R' is an aryl group and R" is hydrogen, lower alkyl or aralkyl.

The alkali metal salts may be derived from potassium, sodium, lithium, etc., with potassium and sodium being particularly preferred. The quarternary ammonium salts may be those such as pyridinium, procaine, N-methylglucamine, ethanolamine or diethanolamine.

The foregoing compounds possess several centers of chirality and are produced by the various processes as various isomeric mixtures. The present invention is directed to compounds of the preferred stereochemical configuration of formula I and to mixtures of it together with its enantiomers.

With respect to those in the penem nucleus itself, the preferred configuration is the carbon atoms at the 5 and 6 positions of the absolute stereochemistry R and S, respectively. The two hydrogen atoms attached to the 5 and 6 carbon atoms are thus trans to one another. The stereochemistry of the C-8 carbon atom may be designated as either R or S depending on the exact nature of the $R_2$ substituent. For instance, the compounds wherein $R_2$ is methyl will have the 8R stereochemistry. The most preferred stereochemical configuration for a compound of this invention wherein $R_2$ is methyl is designated 5R,6S,8R, and has the following representative spatial configuration:

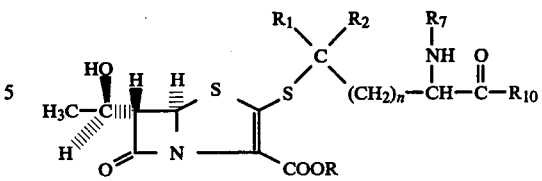

The preferred stereochemical configuration of all the compounds of formula I is that shown in formula Ia; however, the nomenclature may differ depending on the nature of the $R_5$ subsituent. Wherein the $R_5$ group of formula I has a higher priority in the Cahn-Ingold-Prelog system, e.g., a 2-pyridyl group, a compound having the most preferred stereochemical configuration will be designated 5R, 6S, 8S, but be of the same relative spatial configuration at C-5, C-6 and C-8 as the 5R, 6S, 8R compound of formula III. These compounds additionally possess an asymetric center at the carbon atoms to which the $NHR_7$ and $COOR_6$ substituents are attached ("amino acid carbon") depending on the configuration of the starting materials. Most preferably this carbon atom will possess absolute stereochemistry of the R configuration when n is greater than zero, and of the S configuration when n is zero. When naturally occurring amino acids other than cysteine are utilized as starting materials, the amino acid carbon will be of the "R" or "D" and the "S" or "L" configurations. In the case of cysteine, when D-cysteine is the starting amino acid in the synthesis of Ia, the product is designated as having a 2'S configuration by the Cahn-Ingold-Prelog system; conversely, L-cysteine will lead to a product Ia designated as having a 2'R configuration. However, D-homocysteine and its homologs and L-homocysteine and its homologs lead to products Ia designated as 2'R or 2'S, respectively, according to the Cahn-Ingold-Prelog system.

Certain of the processes of this invention produce these compounds as their racemic mixtures, e.g., a 5R,6S,8R compound is produced with its enantiomer (mirror image), i.e., a 5S,6R,8S compound in the equal amounts when the starting compound is a racemic mixture. The two enantiomers may be separated by conventional means, e.g., by resolution by fractional crystallizations of optically active salt forms, e.g.. the salts derived from optically active amino acids (−)-brucine, or (+)- and (−)ephedrine. Alternatively, the compounds may be produced in their pure enantiomeric forms by utilizing optically active intermediates in the synthetic procedure. These optically active intermediates may be produced by conventional resolution or by stereospecific synthesis according to the procedures of Girijavallabhan et.al., U.S. Ser. No. 91,609, entitled "SYNTHESIS OF OPTICALLY ACTIVE INTERMEDIATES FOR PENUM SYNTHESIS", filed Nov. 5, 1979, now abandoned, which are also disclosed in Schering E.P.O. Published Application No. 0013662, the disclosure of both of which are hereby incorporated by reference.

Preferred compounds of formula I are those wherein $R_5$ is a lower alkyl group. Particularly preferred are those compounds of formula I wherein $R_5$ is a methyl group.

A most particularly preferred group of compounds of formula I encompassed by this invention are those wherein $R_5$ is methyl, particularly those wherein $R_{10}$ is $-OR_6$ and the stereochemical configuration is designated 5R,6S,8R. Of these, the compounds wherein the amino acid carbon possesses the R configuration when n is greater than zero and the S configuration when n is zero are most highly preferred. A particularly preferred compound is (5R,6S,8R,2'S)-2-[(2'-amino-2'-carboxyethyl)thio]-6-(1-hydroxyethyl)-2-penem-3-carboxylic acid, sodium salt.

The compounds of this invention possess antibacterial activity of both the gram-positive and gram-negative type. Thus, when tested in standardized microbiological assays, the compounds of this invention are active against such gram-positive organisms as *Staphylococcus epidermidis*, and *Bacillus subtilis*, and such gram-negative organisms as *E. coli*, Pseudomonas and Salmonella at test levels of 0.1 to 100 ug/ml. Additionally, they show activity against such organisms in the presence of penicillanase indicating a resistance to this enzyme and are inhibitors of beta-lactamases. For instance, (5R,6S,8R,2'S)-2-[2'-amino-2'-carboxyethyl)thio]-6-(1-hydroxyethyl)-2-penem-3-carboxylate is active against Salmonella 76061701 at a test level of about 0.25 ug/ml. and against *E. coli* ATCC 10536 at a test level of 0.5 ug/ml.

Thus, the present invention includes within its scope pharmaceutical compositions comprising an antibacterially effective amount of a penem of formula I together with a compatible, pharmaceutically acceptable carrier or coating. Also included within this invention is the method of eliciting an antibacterial response in a warm-blooded animal having a susceptible bacterial infection which comprises administering to said animal a non-toxic, antibacterially effective amount of compound of formula I.

The dosage administered of the penems of this invention is dependent upon the age and weight of the animal species being treated, the mode of administration, and the type and severity of bacterial infection being prevented or reduced. Typically, the dosage administered per day will be in the range of 100-5000 mg, with 500-1000 mg being preferred.

For oral administration, the compounds of this invention may be formulated in the form of tablets, capsules, elixirs or the like. Likewise, they may be admixed with animal feed. They may also be applied topically in the form of ointments, both hydrophilic and hydrophobic, in the form of lotions which may be aqueous, non-aqueous or of the emulsion type, or in the form of creams.

The compounds of formula I may be utilized in liquid form such as solutions, suspensions and the like for otic and optic use and may also be administered parenterally via intramuscular injection.

The compounds of this invention are preparable by a reaction sequence starting with a compound of the formula II

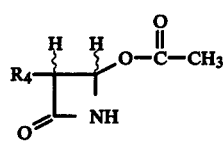

wherein $R_4$ is as hereinbefore defined except that any free hydroxy group is protected by a suitable hydroxy protecting group. This starting material is treated with an anion of the formula

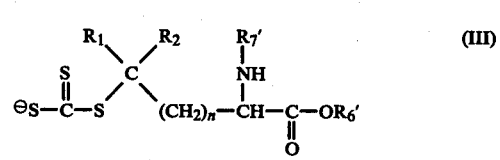

wherein $R_1$, $R_2$ and n are as hereinbefore defined, $R'_6$ is lower alkyl, aryl or aralkyl or another suitable carboxy protecting group, and $R'_7$ is lower alkyl, aryl, aralkyl, or a suitable amino protecting group, to afford the compound of formula IV

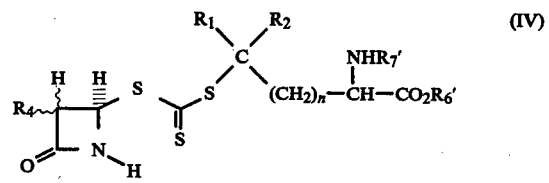

wherein $R_1$, $R_2$, $R'_6$, $R'_7$ and are as hereinbefore defined and $R_4$ is as hereinbefore defined except that any free hydroxy group is protected by a suitable hydroxy protecting group. Preferred amino and carboxy protecting groups are p-nitrobenzyl and allyl with the latter being particularly preferred. Generally, this reaction is conducted by preparing the anion of formula III in situ and then adding the compound of formula II to the aqueous reaction mixture. Typically, the reaction is conducted at room temperature or in the cold.

Alternatively, the intermediate of formula IV may be prepared a reaction sequence which begins with treatment of an optically active compound of the formula V:

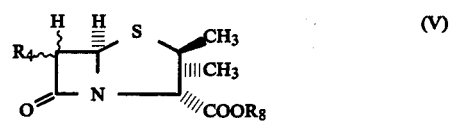

wherein $R_8$ is a lower alkyl or aralkyl group and $R_4$ is as hereinbefore defined except that any free hydroxy group is protected by a suitable hydroxy protecting group, with elemental chlorine, to afford the intermediate of the formula:

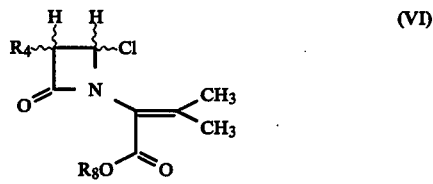

wherein $R_8$ is as hereinbefore defined and $R_4$ is as hereinbefore defined except that any free hydroxy group is protected by a suitable hydroxy protecting group. The step is typically conducted in a suitable organic solvent at temperatures of about $-30°$ to $0°$ C. Particularly suitable solvents are those such as methylene chloride, chloroform, carbon tetrachloride, toluene and xylene. Preferably, a nitrogen atmosphere is also used. The elemental chlorine is typically added as a solution having concentration of 0.5 to 5M in a suitable organic solvent, e.g., carbon tetrachloride.

Ozonolysis of the intermediate of formula VI then affords the intermediate of the formula VII:

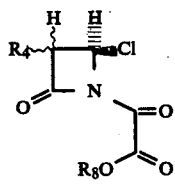
(VII)

wherein $R_8$ is as hereinbefore defined and $R_4$ is as hereinbefore defined except that any free hydroxy group is protected by a suitable hydroxy protecting group. This ozonolysis is typically conducted at low temperatures, e.g., about $-80°$ to about $-40°$ C. in a non-polar, organic solvent. Most preferably, the same solvent is utilized for this step as for the previous step of the instant process. A particularly suitable solvent is methylene chloride but others, such as chloroform, or xylene, may also be used.

Reaction of the intermediate of formula VII with a nucleophile of the formula III results in the compound of formula IV. Typically, this reaction is conducted at temperatures of about $-78°$ C. to room temperatures, with the former being most particularly preferred.

The anion of formula III is prepared in situ by treatment of the compound of the formula

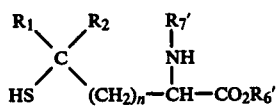
(VIII)

wherein $R_1$, $R_2$, $R'_6$, $R'_7$ and n are as hereinbefore defined with a strong base such as sodium or potassium hydroxide and carbon disulfide. Suitable solvents are those such as methanol, ethanol, isopropanol, etc. Typically the reaction is conducted at room temperature. The thiol of formula VIII is prepared by reduction of the corresponding disulfide. Typically, the reduction is conducted at 0° C. in methanol with zinc-hydrochloric acid.

The nitrogen of the lactam of formula IV is then reacted with an ester of glyoxylic acid to afford the compound of formula IX:

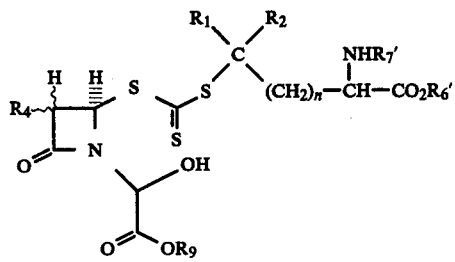
(IX)

wherein $R_1$, $R_2$, $R'_6$, $R'_7$ and n are as hereinbefore defined and $R_4$ is as hereinbefore defined except that any free hydroxy group is protected by a suitable hydroxy protecting group, and $R_9$ is a suitable carboxy protecting group.

In a highly preferred embodiment, the carboxy and amino protecting groups will be allyl and an allyloxycarbonyl group, respectively, so as to provide the intermediates of the formula:

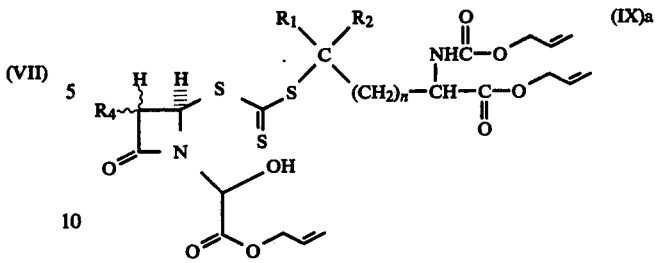
(IX)a wherein $R_1$, $R_2$, and n are as hereinbefore defined and $R_4$ is as hereinbefore defined except that any free hydroxy group is protected by a suitable hydroxy protecting group. This reaction is usually preferably conducted at reflux temperatures in a non-polar aprotic solvent such as tetrahydrofuran or benzene. Reaction times of 2–10 hours are generally typical.

The compound of formula IX is then treated with a chlorinating or brominating agent, e.g., thionyl chloride, methanesulfonyl chloride, thionyl bromide, or phosphorus tribromide, in the presence of an equivalent of an acid acceptor, e.g., pyridine or triethylamine, so as to afford replacement of the hydroxy group in the 1-glyoxylate function so as to produce the compound of formula X:

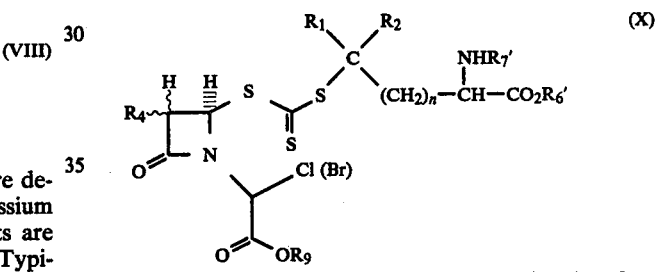
(X)

wherein $R_1$, $R_2$, $R'_6$, $R'_7$, $R_9$ and n are as hereinbefore defined and $R_4$ is as hereinbefore defined except that any free hydroxy group is protected by a suitable hydroxy protecting group. Suitable solvents are those such as methylene chloride, tetrahydrofuran or benzene. Temperatures of about 0°–20° l C. and reaction times of 10–60 minutes are generally preferred.

The chloride or bromide or formula X is then reacted with a suitable phosphine, e.g., tri-p-methoxyphenyl phosphine, tributylphosphine or most preferably, triphenylphosphine to afford the compound of the formula XI:

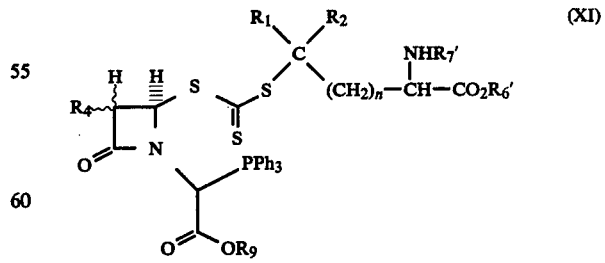
(XI)

wherein $R_1$, $R_2$, $R'_6$, $R_7$, $R'_9$ and n are as hereinbefore defined and $R_4$ is as hereinbefore defined except that any free hydroxy group is protected by a suitable hydroxy protecting group. Typically, the reaction is conducted at room temperature in a polar, aprotic solvent such as hexamethylphosphoramide or dimethylformamide. Reaction times generally vary from about 12–48 hours.

The phosphorane of formula XI is most preferably isolated and then heated to cause cyclization resulting in the compound of formula XII:

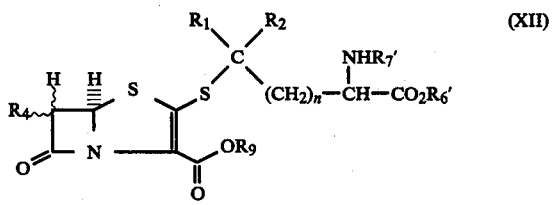

wherein $R_1$, $R_2$, $R'_6$, $R'_7$, $R_9$ and n are as hereinbefore defined and $R_4$ is as hereinbefore defined except that any free hydroxy group is protected by a suitable hydroxy protecting group. The cyclization is generally conducted at reflux temperatures in an organic solvent such as benzene, toluene or xylene under an inert atmosphere, e.g., nitrogen or argon. Reaction times generally vary from 12–48 hours.

Alternatively and preferably, compounds of formula XII are prepared from intermediates of formula IV according to procedures of Adriano Afonso and Frank Hon, U.S. Ser. No. 230,774, filed Feb. 2, 1980 (of common assignee as the instant application) the disclosure of which is hereby incorporated by reference. By this procedure, a compound of formula IV is reacted with an acid halide of formula XIII:

wherein $R_9$ is defined as hereinabove, in an inert solvent in the presence of a tertiary amine and an alkali metal carbonate; followed by reaction of the thereby produced imido derivative of formula XIV:

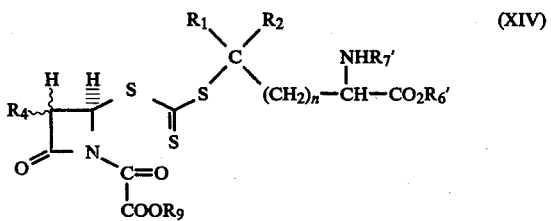

wherein $R_1$, $R_2$, $R'_6$, $R'_7$ and $R_9$ are as hereinbefore defined and $R_4$ is as hereinbefore defined except that any free hydroxy group is protected by a suitable hydroxy protecting group. Treatment of a compound of formula XIV with triethylphosphite in a halogenated solvent yields a cyclized compound of formula XII.

Removal of the protecting groups from the compounds of formula XII results in the products of formula I wherein $R_7$ is hydrogen, acyl, lower alkyl, aryl or aralkyl. The conventional amino protecting groups, e.g., benzyloxycarbonyl, p-nitrobenzyloxycarbonyl and benzhydryloxycarbonyl, and carboxy protecting groups, e.g., benzyl, p-nitrobenzyl and benzhydryl, can be removed by hydrogenation. Certain hydroxy protecting groups such as trichloroethoxycarbonyl may be removed by deprotection via zinc/acetic acid in a suitable aprotic solvent such as tetrahydrofuran. Most preferably, however, the allyl and allyloxycarbonyl protecting groups will be utilized for carboxy and amino groups. This group is most preferably removed by the procedure of Tsuji described in Tetrahedron letters, 7, 613 (1979). The Tsuji deprotection procedure utilizes an amine salt of formic acid and a mixture of a palladium compound and triphenyl phosphine as the catalyst. This deprotection method is particularly suitable for the sensitive beta-lactam carboxylates of this invention.

The amino group of the compounds of formula I wherein $R_7$ is hydrogen may optionally be converted to their corresponding compounds wherein $R_7$ is a Schiff's base, for instance, as in U.S. Pat. No. 4,172,144, or to the compounds wherein $R_7$ is an amidine or guanidine, e.g., where the amino group is converted to the —NH—C=NH group, as described in ICAAC, 11th International Congress of Chemotherapy, 19th Interscience Conference on Antimicrobial Agents and Chemotherapy, Boston, Oct. 1–5, 1979, Papers 231 and 232.

Compound of formula I wherein $R_{10}$ is amino, lower alkylamino, or an 2-amino acid residue are prepared from the corresponding compounds of formula I where $R_{10}$ is —OH utilizing conventional techniques well known in the art.

Compounds preparable by the above reaction schemes include the following representative compounds of this invention each together with its enantiomer when prepared from racemic starting materials, and alone when prepared from chiralintermediates. The most highly preferred stereochemical isomers are named, i.e., the 5R,6S,8R2'S isomers when n is zero, and the 5R,6S,8R2'R isomers when n is 1–4; however, the corresponding isomers may be prepared by choice of suitable starting compounds:

(2'S)-sodium 2-[(2-amino-2'-carboxyethyl)thio]-2-penem-3-carboxylate;

(2'R)-sodium 2-[(2'-amino-2'-carboxypropyl)thio]-2-penem-3-carboxylate;

(2'S)-sodium 2-[(2'-amino-2'-carboxy-3',3'-dimethylethyl)thiol]-2-penem-3-carboxylate;

(2'S)-sodium 2-[(2'-acetylamino-2'-carboxyethyl)thio]-2-penem-3-carboxylate;

(2'S)-sodium 2-[(2'-amino-2'-methoxycarbonylethyl)thiol]-2-penem-3-carboxylate;

(2'S)-sodium 2-[(2'-amino-2'-phenoxycarbonylethyl)thio]-2-penem3-carboxylate;

(2'S)-sodium 2-[(2'-amino-2'-benzyloxycarbonylethyl)-thiol]-2-penem-3carboxylate;

(2'R)-sodium 2-[(2'-amino-2'-carboxybutyl)thiol]-2-penem-3-carboxylate;

(5R,6S,8R,2'S)-2-[(2'-amino-2'-carboxyethyl)thio]-6-(1-hydroxy-ethyl)-2-penem-3-carboxylic acid, pyridinium or sodium salt;

(5R,6S,8R,2'R)-2-[(2'-amino-2'-carboxypropyl)thio]-6-(1-hydroxyethyl)-2-penem-3-carboxylic acid, pyridinium or sodium salt;

(5R,6S,8R,2'S)-2-[(2'-acetylamino-2'-carboxyethyl)thio]-6-(1-hydroxyethyl)-2-penem-3-caboxylic acid, pyridinium or sodium salt;

(5R,6S,8R,2'S)-2-[(2'-amino-2'-methoxycarbonylethyl)-thio]-6-(1-hydroxyethyl)-2-penem-3-carboxylic acid, pyridinium or sodium salt;

(5R,6S,8R,2'S)-2-[(2'-amino-2'-phenoxycarbonylethyl)-thio]-6-(1-hydroxyethyl)-2-penem-3-carboxylic acid, pyridinium or sodium salt;

(5R,6S, 8R,2'S)-2-[(2'-amino-2'-benzyloxycarbonylethyl)thio]-6-(1-hydroxyethyl)-2-penem-3-carboxylic acid, pyridinium or sodium salt;

(5R,6S,8R,2'S)-2-[(2'-amino-2'-carboxy-3',3'-dimethylethyl)-thio]-6-(1-hydroxyethyl)-2-penem-3-carboxylic acid, pyridinium or sodium salt;

(5R,6S,8R,2'R)-2-[(2'-amino-2'-carboxy-4'-methylpropyl)thio]-6-(1-hydroxyethyl)-2-penem-3-carboxylic acid, pyridinium or sodium salt;

(5R,6S,8R,2'R)-2-[(2'-amino-2'-carboxybutyl)thio]-6-(1-hydroxyethyl)-2-penem-3-carboxylic acid, pyridinium or sodium salt;

(5R,6S,8R,2'S)-2-[(2-'methylamino-2'-carboxyethyl)thio]-6-(1-hydroxyethyl)-2-penem-3-carboxylic acid, pyridinium or sodium salt;

(5R,6S,8R,2'S)-2-[(2'-phenylamino-2'-carboxyethyl)thio]-6-(1-hydroxyethyl)-2-penem-3-carboxylic acid, pyridinium or sodium salt;

(5R,6S,8R,2'S)-2-[(2'-benzylamino-2'-carboxyethyl)thio]-6-(1-hydroxyethyl)-2-penem-3-carboxylic acid, pyridinium or sodium salt;

(5R,6S,8R,2'S)-2-[(N-ethoxycarbonyl-2'-amino-2'-carboxyethyl)-thio]-6-(1-hydroxyethyl)-2-penem-3-carboxylic acid pyridinium or sodium salt;

(5R,6S,8R,2'S)-2-[(N-2,2,2-trifluoroacetyl-2'amino-2'-carboxyethyl)thio]-6-(1-hydroxyethyl)-2-penem-3-carboxylic acid, pyridinium or sodium salt;

(5R,6S,8R,2'S)-2-[(N-guanidino-2'-amino-2'-carboxyethyl)thio]-6-hydroxyethyl)-2-penem-3-carboxylic acid, pyridinium or sodium salt;

(5R,6S,8R,2'S)-2-[(N-trichloroethoxycarbonyl-2'-amino-2'-carboxyethyl)thio]-6-(1-hydroxyethyl)-2-penem-3-carboxylic acid, pyridinium or sodium salt;

(5R,6S,8R,2'S)-2-[(N-t-butoxycarbonyl-2'amino-2'-carboxyethyl)-thio]-6-(1-hydroxyethyl)-2-penem-3-carboxylic acid, pyridinium or sodium salt;

(5R,6S,8R,2'S)-2-[(N-p-nitrobenzoxycarbonyl-2'-amino-2'-carboxyethyl)thio]-6-(1-hydroxyethyl)-2-penem-3-carboxylic acid, pyridinium or sodium salt;

(5R,6S,8R,2'S)-2-[(N-benzyloxycarbonyl-2'-amino-2'-carboxyethyl)thio]-6-(1-hydroxyethyl)-2-penem-3-carboxylic acid, pyridinium or sodium salt;

(5R,6S,8R,2'S)-2-[(N-3''-methyl-2''-butenoatemethylester-2'-amino-2'-carboxyethyl)thio]-6-(1-hydroxyethyl)-2-penem-3-carboxylic acid, pyridinium or sodium salt;

(5R,6S,8R,2'S)-2-[(N-1-(3-oxocyclohex-1-enyl)-2'-amino-2'-carboxyethyl)thio]-6-(1-hydroxyethyl)-2-penem-3-carboxylic acid, pyridinium or sodium salt;

(5R,6S,8R,2'S)-2-[(N-2-(4-oxopent-2-enyl)-2'-amino-2'-carboxyethyl)thio]-6-(1-hydroxyethyl)-2-penem-3-carboxylic acid, pyridinium or sodium salt;

(5R,6S,2'S)-sodium-2-[(2'-amino-2'-carboxyethyl)thio]-6-ethyl-2-penem-3-carboxylate;

(5R,6S,8R,2'R)-sodium-2-[(2'-amino-2'-carboxyethyl)-thio]-6-(1-hydroxypropyl)-2-penem-3-carboxylate;

(5R,6S,8S,2'S)-sodium-2-[(2'-amino-2'-carboxyethyl)-thio]-6-[1-hydroxy-1-(4-pyridyl)methyl]-2-penem-3-carboxylate;

(5R,6S,8R,2'S)-sodium-2-[(2'-amino-2'-carboxyethyl)-thio]-6-(alpha-hydroxybenzyl)-2-penem-3-carboxylate;

(5R,6S,8S,2'S)-sodium-2-[(2'-amino-2'-carboxyethyl)-thio]-6-[1-hydroxy-2-(2-thienyl)ethyl]-2-penem-3-carboxylate;

(5R,6S,8R,2'R)-2-[(2'-acetylamino-2'-carboxypropyl)-thio]-6-(1-hydroxyethyl)-2-penem-3-carboxylic acid, pyridinium or sodium salt;

(5R,6S,8R,2'R)-2-[(2'-amino-2'-methoxycarbonylpropyl)thio]-6-(1-hydroxyethyl)-2-penem-3-carboxylic acid, pyridinium or sodium salt; and (5R,6S,8R,2'S)-2-[(2'-N-D-alanyl-2'-amino-2'-carboxyethyl)thio]-6-(1-hydroxyethyl)-2-penem-3-carboxylic acid, pyridinium or sodium salt.

(5R,6S,8R,2'S,2''R)-2-[(2'-amino-2'-(2''-carboxyethyl)-carbamoylethyl]thio)-6-(1-hydroxyethyl)-2-penem-3-carboxylic acid pyridinium or sodium salt;

(5R,6S,8R,2'S)-2-[(2'-amino-2'-carbamoylethyl)-thio]-6-(1-hydroxyethyl)-2-penem-3-carboxylic acid pyridinium or sodium salt;

(5R,6S,8R,2'S)-2-[(N-ethoxycarbonyl-2'-amino-2'-methoxycarbonylethyl)thio]-6-(1-hydroxyethyl)-2-penem-3-carboxylic acid pyridinium or sodium salt.

This same series can also be prepared in the following configurations when n is zero or (5R,6S,8R,2'S) when n is greater than zero, (5R,6S,8S,2'R) when n is zero or (5R,6S,8S,2'S) when n is greater than zero, (5R,6S,8S,2'S) when n is zero or (5R,6S,8S,2'R) when n is greater than zero, or (5R,6S,8R,2'R).

The following preparations describe in detail the compounds of the present invention and processes for their preparation. It will be apparent to those skilled in the art that many modifications, both of materials and methods, may be practiced without departing from the spirit and scope of the invention. Throughout these preparations and examples, "NMR" denotes nuclear magnetic resonance spectra; "rotation" denotes optical rotation of the compounds in a suitable solvent; "MS" denotes mass spectra; "UV" denotes ultraviolet spectra; and "IR" denotes infrared spectra. Chromatography is performed on silica gel unless otherwise denoted.

PREPARATION A

To a solution of 100 g 6-β-aminopenicillanic acid in 1200 ml 2.5 N sulfuric acid is added 150 g sodium bromide. To the stirred solution at 0° C. is added simultaneously 40 g sodium nitrite in 150 ml water and 40 ml bromine. The addition is completed in 10 minutes, maintaining the temperature at 0° to 5° C. The mixture is then stirred rapidly for 1 hour, then filtered. The filter cake is washed with water and taken up in 600 ml ethyl acetate. The ethyl acetate solution is washed with water, cold dilute sodium bisulfite solution and then again with water. After drying over anhydrous sodium sulphate, the solvent is removed under vacuum to afford 67 g in 85:15 ratio (by NMR data) of 6,6-dibromopenicillanic acid and 6-bromopenicillanic acid. IR: 1728 cm$^{-1}$ and 1800 cm$^{-1}$ (chloroform solution) NMR: =5.7, 1H, s; =4.5, 1H, s; =1.55–1.67, 6H (CDCl$_3$).

PREPARATION B

To a solution of 67 g in 85:15 ratio of 6,6-dibromopenicillanic acid to 6-bromopenicillanic acid in 500 ml dimethylformamide at 0° C. is added 37.3 g finely powdered potassium carbonate. The solution is stirred 5–10 minutes and 38.3 g methyl iodide is added. The reaction mixture is then stirred for 2 hours allowing the temperature to come to ambient. The reaction is followed by thin layer chromatography eluting with methylene chloride. When complete, the reaction is decanted and the solvent removed under high vacuum to leave 100 ml of solution. To this is added 600 ml and 38.3 g methyl iodide is added. The reaction mixture is then stirred for 2 hours allowing the temperature to come to ambient. The reaction is followed by thin layer chromatography eluting with methylene chloride. When complete, the reaction is decanted and the solvent removed under high vacuum to leave 100 ml of solution. To this is added 600 ml ethyl acetate. The solution is then washed with water, dried over anhydrous sodium sulphate and concentrated under vacuum to afford 63 g crude methyl ester. Subsequently, 48 g of pure methyl 6,6-dibromopenicillanate is isolated from this crude product by high pressure liquid chromatography eluting with methylene chloride.

NMR: =5.7, 1H, s; =4.48, 1H, s; =3.73, 3H, s; =1.42, 3H, s; =1.59, 3H, s (CDCl$_3$).

PREPARATION C

To a solution of 13.7 g methyl 6,6-dibromopenicillanate in 250 ml dry tetrahydrofuran at −78° C. under nitrogen is added 14.7 ml of 3M methyl magnesium bromide in ethyl ether. After stirring for 30 minutes at −78° C., 8 g of freshly distilled acetaldehyde is added and stirring continued for 45 minutes. The reaction mixture is warmed to −20° C. at which time 50 ml 1 M potassium phosphate monobasic is added and stirring continued for 5 minutes. The reaction mixture is then poured into 1 liter cold ethyl acetate and washed once with 150 ml brine solution and twice with 150 ml water. The ethyl acetate layer is separated, dried over anhydrous sodium sulfate and evaporated under vacuum. The products, methyl 6-bromo-6-(1-hydroxyethyl)-penicillanate and methyl 6-bromo-6-(1-hydroxyethyl) penicillanate, are detected by thin layer chromatography eluting with 10% ethyl acetate/chloroform.

PREPARATION D

To a solution of 8.0 g methyl 6-bromo-6-(1-hydroxyethyl)penicillanate in 200 ml 95% ethanol is added 800 mg 10% palladium on calcium carbonate. The solution is shaken under 30 lbs hydrogen pressure for 5 hours. Disappearance of starting material is followed by thin layer chromatography eluting with 20% ethyl acetate/-chloroform. The catalyst is filtered and 100 ml 1 M potassium phosphate buffer at pH 7 is added. The precipitate formed is filtered and washed with ethanol. The ethanol is removed under vacuum and 200 ml ethyl acetate added. After washing twice with 50 ml water, and drying over anhydrous sodium sulfate, the ethyl acetate is removed under vacuum to afford a crude mixture of methyl 6-(1-hydroxyethyl)penicillanate. Column chromatography of 18. g of said mixture eluting with 20% ethyl acetate affords 6.4 g methyl (5R,6S,8R)-6-(1-hydroxyethyl)-penicillanate.

NMR: =2.4–2.7, 1H, d; =4.41, 1H, s; =3.74, 3H, s; =3.2–3.33, 1H; =1.25–1.35, 3H, d; =1.44, 3H, s; =1.16, 3H, s (CDCl$_3$).

PREPARATION E

To a solution of 6.2 g methyl (5R,6S,8R)-6-(1-hydroxyethyl)penicillanate in 60 ml. dry methylene chloride at 0° C. under nitrogen is added 3.8 ml pyridine then 3.3 ml β,β,β-trichloroethylchloroformate. The reaction is stirred 15 minutes until all starting material is reacted (as determined by thin layer chromatography with 20% ethyl acetate/chloroform). The solution is poured into 250 ml cold methylene chloride and washed twice with cold 10% phosphoric acid solution, once with cold dilute sodium bicarbonate, and then with water. After drying over anhydrous sodium sulfate, the solvent is removed under vacuum to afford 10.0 g methyl (5R,6S,8R)-6-(1-trichloroethoxycarbonyloxyethyl)-penicillanate.

NMR: =5.13–5.16, 1H, d; =4.78, 2H, s; =4.43, 1H, s; =3.76, 3H, s; =3.38–3.58, 1H; =1.45–1.63, 9H; (CDCl$_3$).

PREPARATION F

A. To a solution of 9.1 g methyl (5R,6S,8R)-6-(1-trichloroethoxycarbonyloxyethyl)penicillanate in 350 ml distilled methylene chloride at −20° C. under nitrogen is added 62.3 ml of 1 M chlorine/carbon tetrachloride solution. The reaction is stirred for 15 minutes at about −20° C. (until found to be complete by thin layer chromatography eluting with chloroform). The solution is evaporated under vacuum to afford 10.0 g of product comprising (3S,4R,5R)-1-[(2-methyl-1-methoxycarbonyl)prop-1-enyl]-3-(1-trichloroethoxycarbonyloxyethyl)-4-chloroazetidin-2-one.

IR: 1720, 1770–1790 cm$^{-1}$ (chloroform solution)

NMR: =5.79–5.81, 1H, d; =4.75, 2H, s; =3.74, 3H, s; =2.27, 3H, s; =2.0, 3H, s; =1.45–1.54, 3H, d (CDCl$_3$).

B. Through a solution of 7.7 g crude (3S,4R,5R)-1-[2-methyl-1-methoxycarbonyl-prop-1-enyl]-3-(1-trichloroethoxycarbonyloxyethyl)-4-chloroazetidin-2-one in 250 ml methylene chloride at about −78° C. is passed ozone for 45 solution is poured into 250 ml cold methylene chloride and washed twice with cold 10% phosphoric acid solution, once with cold dilute sodium bicarbonate, and then with water. After drying over anhydrous sodium sulfate, the solvent is removed under vacuum to afford 10.0 g methyl (5R,6S,8R)-6-(1-trichloroethoxycarbonyloxyethyl)penicillanate.

NMR: =5.13–5.16, 1H, d; =4.78, 2H, s; =4.43, 1H, s; =3.76, 3H, s; =3.38–3.58, 1H; =1.45–1.63, 9H; (CDCl$_3$). minutes. (Disappearance of starting material is followed by thin layer chromatography eluting with chloroform). The reaction is allowed to sit for 1 hour at −78° C. with excess ozone. Nitrogen is then bubbled in for 3–5 minutes and then 3 ml dimethylsulfide is added. The solution is allowed to warm to ambient temperature and held for 2 hours. Nitrogen is bubbled through the solution to remove excess dimethylsulfide. Optionally, the solvent may be removed and the residue purified by chromatography to afford (3S,4R,5R)-[1-(2-methoxy-1,2-dioxoethyl)]-3-(1-trichloroethoxycarbonyloxyethyl)-4-chloroazetidin-2-one.

NMR: =5.97–6.0, 1H, d; =5.76, 2H, s; =4.93, 2H, s; J=1 c/s, =1.45–1.55, 3H, d.

PREPARATION G

By substantial repetition of the process described in Preparations A–F, utilizing the appropriate starting materials, the following compounds of the formula

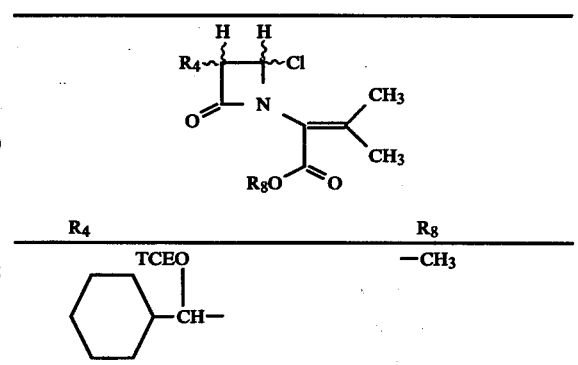

-continued

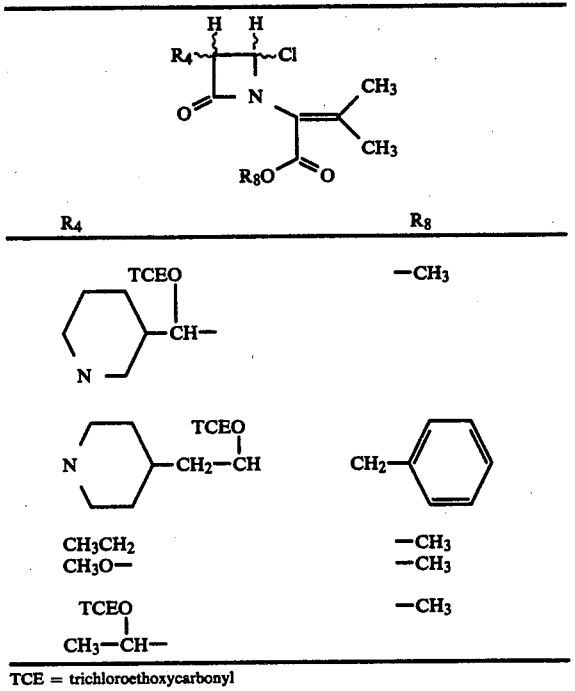

TCE = trichloroethoxycarbonyl

PREPARATION H

Bis (N-allyloxy carbonyl)-L-cystine bis-allyl ester

A solution of L-cystine (12 g) in a 4N sodium hydroxide (25 ml) at ice bath temperature is stirred while allyl chloroformate (10.6 ml) and 4N sodium hydroxide (25 ml) are added dropwise. The mixture is stirred for 30 mins. after the final addition and is then washed with 50 ml of ether. The aqueous phase is then acidified to pH 2 with 1N hydrochloric acid and extracted with 3×50 ml ether. The ether extracts are dried with sodium sulfate and evaporated. The residual colorless oil is dissolved in acetone (75 ml) containing triethylamine (9.6 ml) and stirred while allyl bromide (6.0 ml) is added dropwise. The mixture is stirred overnight, diluted with ethylacetate (75 ml) and brine (75 ml). The aqueous phase is extracted three times with ethyl acetate. The organic extracts are washed with 1N sodium hydroxide, 1N hydrochloric acid, water, dried with sodium sulfate and evaporated. The title product is crystallized from ether-hexane as colorless needles, with a m.p. of 47°–48° C. and an $[\alpha]_D$ of +55° (chloroform).

PREPARATION I

N-allyloxycarbonyl-L-cysteine allyl ester

A suspension of zinc dust (8 g) in a solution of bis (N-allyloxylcarbonyl)-L-cystine bis allyl ester (7.56 g) in methanol (50 ml) at 0° C. is stirred vigorously while adding concentrated hydrochloric acid (5 ml) in one portion. After 2 minutes the mixture is diluted with ice water and extracted with 3×50 ml of chloroform. The extracts are dried over sodium sulfate and evaporated under reduced pressure to afford the title product.

PREPARATION J

Bis (N-allyloxycarbonyl)-D-cysteine bis allyl ester

Following the procedure described in Preparation H utilizing D-cysteine as starting material there is obtained the title product, having a melting point of 48°–49° C. and an $[\alpha] = -55°$ (chloroform).

PREPARATION K

N-allyloxycarbonyl-D-cysteine allyl ester

A suspension of zinc dust (5.18 g) in a solution of bis(N-allyloxycarbonyl)-D-cysteine bis-allyl ester (5.18 g) in methanol (50 ml) at 0° C. is stirred vigorously while adding concentrated hydrochloric acid (3.5 ml) in one portion. After two minutes, the mixture is worked up as in the above Preparation I to afford the title product.

PREPARATION L

N-allyloxycarbonylsulfanyl-D-cysteine allyl ester

A solution of D-cysteine (12 g) in 4N sodium hydroxide (25 ml) is stirred at 0° while N-allylloxycarbonylsulfanilyl chloride (30 g) and 4N sodium hydroxide (25 ml) is added dropwise. The mixture is stirred for 30 minutes, acidified with 1N hydrochloric acid, extracted with ether and the extract evaporated. The residual oil is dissolved in acetone (75 ml) containing triethylamine (9.6 ml) and stirred while allyl bromide (6.0 ml) is added dropwise. This mixture is stirred overnight, diluted with ethyl acetate and the organic layer is washed with 1N sodium hydroxide, 1N hydrochloric acid, brine, dried over sodium sulfate and evaporated to afford bis N-allyloxycarbonylsulfanyl-D-cystine bis allyl ester. Treatment of ths bis compound with zinc dust according to the procedure of Preparation I affords the title compound.

PREPARATION M (N-methyl-N-allyoxycarbonyl)-D-cysteine allyl ester

A solution of bis (N-allyloxycarbonyl)-D-cystine bis allyl ester (4.8 g) in dimethyl sulfoxide (40 ml) is added to a solution of sodium hydride (0.5 g) in dimethylsufloxide (40 ml). The reaction is stirred under nitrogen while adding methyliodide (5ml). After 15 minutes the mixture is diluted with ice/water, extracted with ethylacetate and extracts are washed with brine, dried over sodium sulfate and evaporated to afford bis (N-methyl-N-allyloxycarbonyl)-D-cystine bis allyl ester. Treatment of this bis compound according to the procedure of Preparation I affords the title compound.

PREPARATION N

N-acetyl-D-cysteine allyl ester

A solution of bis-N-acetyl D-cystine (3.2 g) in acetone (30 ml) containing triethylamine (4.0 g) is stirred with allyl bromide (4 ml) for 24 hours. The mixture is diluted with water, washed with 1N sodium hydroxide, 1N hydrochloric acid, brine, dried over sulfate and evaporated to afford bis N-acetyl-D-cystine bis allyl ester. Treatment of this bis compound according to the procedure of Preparation I affords the title compound.

EXAMPLE 1

A. The N-allyloxycarbonyl-L-cysteine allyl ester (prepared as in Preparation I) is dissolved in ethanol (170 ml) and to this solution is added with stirring 1N sodium hydroxide (30.9 ml) followed after 1 minute by carbon disulfide (30 ml). The resulting yellow solution is stirred for 1 minute and 4-acetoxyazetidin-2-one (3.00 g) is added in one portion. After 2 minutes the reaction mixture is diluted with ice-water and is extracted with 4×50 ml chloroform. The extract is dried over sodium sulfate and evaporated under reduced pressure. The residue is crystallied from ethyl acetatehexane to afford 4-[(2'(R)-allyloxycarbonylamino-2'-carboxyethylthio allyl ester)carbonothioylthio]azetidin-2-one as yellow needles (5 g) m.p. 107°-108° C. with the following spectra:

IR: 5-62, 5.81, u;
UV: 235 m,u (2900); 300 (11900);
NMR: 2.95 (1H,dd, J=15, 3 cps); 3.86 (1H,dd,J=15, 5 cps)
3.86 (2H,m).

B. A solution of 4-[(2'(R)-allyloxycarbonylamino-2'-carboxyethylthio allyl ester)carbonothioylthio]azetidin-2-one (5.7 g) and allylglyoxylate (2.06 g) in benzene (50 ml) is refluxed for 90 minutes, cooled to room temperature, diluted with ether (50 ml), washed with water (2×25 ml), dried over sodium sulfate and evaporated under reduced pressure. The resulting 1-(allyloxycarbonylhydroxymethyl)-4-[(2'-(S)-allyloxycarbonylamino-2'-carboxyethylthio allyl ester)carbonothioylthio]azetidin-2-one is dissolved in methylene chloride (50 ml). The solution is cooled to 0° C. and chlorosulfonylchloride (1.68 ml) followed dropwise by triethylamine (3.01 ml) are added with stirring. After 15 minutes, the reaction mixture is diluted with ether (50 ml) and washed sucessively with dilute hydrochloric acid, water and brine. The organic layer is filtered thru a silica gel column (30 g) and this column is washed with methylene chloride until the effluent is colorless. The column washings are evaporated under reduced pressure and the resulting 1-(allyloxycarbonylchloromethyl)-4-[(2'(R)-2-allyloxycarbonylamino-2'-carboxyethylthio allyl ester)carbonothioylthio]azetidin-2-one is dissolved in dimethylformamide (30 ml) followed by addition of triphenylphosphine (5.7 g). The reaction mixture is allowed to stand 16 hours at room temperature under nitrogen, and is then diluted with ethylacetate (100 ml), ether (100 ml) and 10% sodium bicarbonate (50 ml). The organic layer is washed with 10% sodium bicarbonate, water, brine, dried over sodium sulfate and concentrated to 100 ml and chromatographed on 200 g silica gel. The column was eluted with ether. Fractions that were homogeneous by t.l.c. (40% ethylacetate-hexane) are combined to afford 1-(allyloxycarbonyl[triphenylphosphoranyl]methyl)-4-[(2'(R)-allyloxycarbonylamino-2'-carboxyethylthio allyl ester)-carbonothioylthio]azetidin-2-one (5.7 g) as a yellow powder with the following spectra:

IR: 5.72, 5.82 u;
UV: 301 m,u (13300).

C. A solution of phosphorane prepared in paragraph B (2 g) in benzene (100 ml) if refluxed for 48 hrs. and then evaporated under reduced pressure. The product is chromatographed on 60 g silica gel. Elution with 40% ethylacetatehexane affords allyl 2-[(2'(R)-2'-allyloxycarbonylamino-2'-carboxyethylthio allyl ester)]-2-penen-3-carboxylate as a colorless oil with the following spectra:

IR: 5.55, 5,80 u; UV: 256 m,u (4500); 330 m,u (5000); NMR: 3.4 (1H, dd, J=15, 2 cps); 3.8 (1H,dd,J=15, 4 cps); 3.5 (2H,m); MS: M±454.

D. To a solution of the allyl ester prepared in paragraph C (0.2 g) in methylene chloride (6 ml) and 1 M pyridinium formate in methylene chloride (6 ml) is added tetra (triphenylphosphine) palladium (100 mg) and triphenylphosphine (100 mg). The solution is stirred under nitrogen for 4 hours. The precipitate formed is collected by centrifugation and resuspended in methylene chloride centrifuged three times. The washed precipitate, 2-[(2'R)-(2'-amino-2'-carboxyethyl)thio]-2-penem-3-carboxylate, pyridinium salt, is then stirred for 5 minutes in 0.5 M sodium 2-ethylhexanoate (2 ml) and washed by centrifugation with ethylacetate, followed by ether and dried to afford sodium 2-[(2'R)-(2'-amino-2'-carboxyethyl)thio]-2-penem-3-carboxylate as a pale tan powder, having an IR: 5.62, 6.22 u.

EXAMPLE 2

A.

(3S,4R,5R)-3-[1'-Trichloroethoxycarbonyloxyethyl]-4-[(2'(S)allyloxycarbonylamino-2'-carboxyethylthio allyl ester)carbonothioylthio]azetidin-2-one N-Allyloxycarbonyl-D-cysteine allyl ester (prepared as in Preparation K) is dissolved in ethanol (130 ml) and to this solution is added with stirring 1N NaOH (20.8 ml) followed after one minute by carbon disulfide (26 ml). The resulting yellow solution is stirred for two minutes, cooled to −78° C. and added in one lot to a precooled solution (−78° C.) of (3S,5R)-3-(1'-trichloroethoxycarbonyloxyethyl)-4-chloro-1-methyloxalylazetidin-2-one (4.26 g) in ethanol (60 ml). The reaction mixture is stirred at −78° C. until thin layer chromatography (40% ethylacetate/hexane) indicates completion of reaction. The reaction mixture is then diluted with ice/water, extracted with ethyl acetate several times and the extracts are washed with brine, dried over sodium sulfate and evaporated under reduced pressure. The crude product is chromatographed on silica gel (90 g). Elution with 20% ethyl acetate/hexane affords the title compound as a yellow resin, IR: (nujol) 5.6, 5.7, 5.8 u; $[\alpha]_D^{26}$+139° (chloroform); NMR (CDCL$_3$) 1.5 (d, 3H, J=6 cps); 3.42 (dd, 1H, J=2.7 cps); 5.65 (d, 1H, J=2 cps).

B.

Allyl-(3S,4R,5R)-3-[(1'-trichloroethoxycarbonyloxyethyl)-4-[2'(S)allyloxycarbonylamino-2'-carboxyethyl thioallyl ester carbonothioylthio]-2-azetidinon-1-yl-2''-triphenylphosphine acetate By treating the compound of Example 2A according to the procedure of Example 1B, the title compound is obtained as a yellow glass, $[\alpha]_D$+100.3° (chloroform)
IR: 5.68, 5.80 u.

C.

Allyl-(5R,6S,8R)-2-[2'-(S)allyloxycarbonylamino-2'-carboxyethylthio allyl ester]-6-(1'-trichloroethyoxycarbonyloxyethyl)-2-penem-3-carboxylate Allyl-(3S,4R,5R)-3-(1'-trichloroethoxycarbonyloxyethyl)-4-[2'(S)-allyloxycarbonylamino-2'-carboxyethyl thio allyl ester) carbono-thioylthio]-2-azetidinon-1-yl-2''-triphenylphosphine acetate (18 g) in benzene (150 ml) is refluxed for nine days, evaporated and chromatographed on silica gel (30 g). Elution with 20% ethylacetate/hexane affords the title compound (0.92 g) as colorless oil, having $[\alpha]_D$+111.6° (chloroform);

IR: (nujol) 5.58, 5.70, 5.80 u; and NMR (CDCl$_3$): 1.55 (d,3H,J=7 cps); 3.45 (d,2H,J=5 cps); 3.90 (dd, 1H, J=2.0 cps); 5.65 (d, 1H, J=2 cps).

D. Allyl-(5R,6S,8R)-2-8 2'(S)allyloxycarbonylamino-2'-carboxyethylthio allyl ester]-6-(1-hydroxyethyl)-2-penem-3-carboxylate To a solution of allyl-(5R,6S,8R)-2-[2'(S)allyoxycarbonylamino-2'-carboxyethylthio allyl ester]-6-(1-trichloroethoxycarbonyloxyethyl)-2-penem-3-carboxylate (0.82 g) in a mixture of tetrahydrofuran (8 ml), water (1.5 ml) and glacial acetic acid (4 ml) cooled to $-20°$ C., is added zinc dust in three lost ($3 \times 300$ mg) during 15 minutes intervals. The reaction mixture is stirred at $-20°$ C. for $3\frac{1}{2}$ hours, diluted with ethyl acetate, filtered and washed with brine, then with brine and 10% sodium bicarbonate solution, again with brine, dried over sodium sulfate and evaporated. The residue is crystallized from ether-hexane as colorless rosettes, (0.52 g) to give the title product having a m.p. of 107°–109° C., an $[\alpha]_D = +102$ (chloroform), and NMR (CDCl$_3$): 1.35 (d, 3H, J=6 cps); 3.46 (d, 2H, J=5 cps); 3.70 (dd, 1H, J=2,7 cps); 5.60 (d, 1H, J=2 cps).

E. Pyridinium (5R,6S,8R,2'S)-2-[2'-amino-2'-carboxyethyl)thio]-6-(1-hydroxyethyl)-2-penem-3-carboxylate A solution of the title compound of paragraph D (100 mg) in 1 M pyridinium formate solution in dichloromethane (3 ml) and 1 M pyridine in dichloromethane (0.25 ml) is stirred under nitrogen. To this solution is added triphenylphosphine (85 mg) and tetrabis (triphenylphosphine)palladium (85 mg). The reaction mixture is stirred at room temperature for 1.5 hours and this precipitate of the title compound is isolated by centrifuging and washing with methylene chloride, ether, as a light tan powder (75 mg), having $[\alpha]_D + 123°$(84% ethanol); IR: (nujol) 5.60, 6-1 u ; and NMR: (d$_6$DMSO): $\delta$1.15 (d,3H,J=6 cps); 3.75 (dd, 1H,J=1.5,7 cps); 5.68 (d,1H,J=1.5 cps).

F. Sodium (5R,6S,8R,2'S)-2-[2'-amino-2'-carboxyethylthio]-6-(1-hydroxyethyl)-2-penem-3-carboxylate A suspension of the title compound of pargraph D (75 mg) is stirred for five minutes in 0.5 M ethyl acetate solution of sodium 2-ethylhexanoate (2 ml) and washed by centrifugation with ethyl acetate followed by ether and dried to afford the title compound as a pale tan powder, having; IR: 5.60, 6.2 u.

EXAMPLE 3
Pyridinium (5R,6S,8R,2'R)-2-[(2'-amino-2'-carboxyethyl)thio]-6-(1-hydroxyethyl)-2-penem-3-carboxylate By following the procedures of paragraphs A-E of Example 2, but utilizing N-allyloxycarbonyl-L-cysteine allyl ester as starting compound, the title compound is obtained as a light tan powder, having:

IR: 5.63, 6-1 u; $[\alpha]_D^{26} + 118°$ (60% ethanol).

EXAMPLE 4
(5R,6S,8R,2'S)-2-[(2'-acetimidoyl-2'-carboxyethyl)thio]-6-(1-hydroxyethyl)-2-penem-3-carboxylate disodium salt A solution of pyridinium (5R,6S,8R,2'S)-2-[(2'-amino-2'-carboxyethyl)thio]6-(1-hydroxyethyl)-2-penem-3-carboxylate (75 mg) in 0.5M sodium 2-ethylhexanoate in water (2 ml) is treated with ethylacetimidate (100 mg) at 20° C. The solution is chromatograhed on Dowex 50×4 (Na+ form), eluted with water, and fractions containing title compound are lyophilized to give the title compound with IR: 5.60 u.

EXAMPLE 5
(5R,6S,8R,2'S)-2-[(2'-guanidoyl-2'-carboxyethyl)thio]-6-(1-hydroxyethyl)-2-penem-3-carboxylate disodium salt A solution of pyridinium (5R,6S,8R,2'S)-2-[(2'-amino-2'-carboxyethyl)thio]-6-(1-hydroxyethyl)-2-penem-3-carboxylate (75 mg) in 0.5M sodium 2-ethylhexanoate in water (2 ml) and and S-benzylisothiourea hydrochloride (50 mg) is stirred at room temperature. The solution was chromatographed on Amberlite 401-S (sodium form), eluted with water and fractions containing title compound are lyophilized to give the title compound with IR: 5.60 u.

EXAMPLE 6
(5R,6S,8R,2'S)-2-[(2'-(ethyl-3''-aminoyl-but-2''-enoate)-2'-carboxyethyl thio]-6-(1-hydroxyethyl)-2-penem-3-carboxylate disodium salt A solution of pyridinium (5R,6S,8R,2'S)-2-[(2'-amino-2'-carboxyethyl)thio]-6-(1-hydroxyethyl)-2-penem-3-carboxylate (100 mg) in 0.5M sodium 2-ethyl hexanoate in water (0.5 ml) and ethyl acetoacetate (130 mg) is stirred at room temperature for several hours and then washed with ethyl acetate. The aqueous layer, upon lyophilization, affords the title compound having IR: 5.60 u.

EXAMPLE 7
(5R,6S,8R,2'S)-2-[(2'-sulfanilamidoyl-2'-carboxyethyl)-thio]-6-(1-hydroxyethyl)-2-penem-3-carboxylate sodium salt Using N-allyloxycarbonylsulfanyl-D-cysteine allyl ester, the procedures of paragraphs A-F of Example 2 are repeated to afford the title compound.

EXAMPLE 8
(5R,6S,8R,2'S)-2-[(2'-benzazamethinyl-2'-carboxyethyl)thio]-6-(1-hydroxyethyl)-2-penem-3-carboxylate disodium salt A solution of pyridinium (5R,6S,8R,2'S)-2-[(2'-amino-2'-carboxyethyl)thio]-6-(1-hydroxyethyl)-2-penem-3-carboxylate (100 mg) in 0.5M sodium 2-ethylhexanoate in methanol (0.5 ml) and benzaldehyde (200 mg) is stirred at room temperature for several hours, diluted with water, washed with ethyl acetate and the aqueous layer is lyophilized to afford the title compound.

EXAMPLE 9
(5R,6S,8R,2'S)-2-[(2'-methylamino-2'-carboxyethyl)thio]-6-(1-hydroxyethyl)-2-penem-3-carboxylate sodium salt Repetition of the procedure detailed in paragraphs A-F of Example 2 utilizing (N-methyl-N-allyloxycarbonyl)-D-cysteine allyl ester affords the title compound.

EXAMPLE 10

(5R,6S,8R,2'S)-2-[(N-carbobenzyloxy-2'-amino-2'-carboxyethyl thio]-6-(1-hydroxyethyl)-2-penem-3-carboxylate disodium salt A solution of pyridinium (5R,6S,8R,2'S)-2-[(2'-amino-2'-carboxyethyl)thio]-6-(1-hydroxyethyl)-2-penem-3-carboxylate (100 mg) in 0.5M sodium 2-ethylhexanoate (2 ml) is stirred at 0° C. with benzylchloroformate (0.2 ml). The reaction is washed with ethyl acetate and aqueous solution is chromatographed on Amberlite 401-S (sodium form). Fractions containing the title compound are lyophilized to give the pure title compound.

EXAMPLE 11

(5R,6S,8R,2'S)-2-[(2'-acetylamino-2'-carboxyethylthio]-6-(1-hydroxyethyl)-2-penem-3-carboxylate disodium salt Substantial repetition of the procedure of paragraphs A-F of Example 2 utilizing N-acetyl-D-cystine allyl ester affords the title compound.

EXAMPLE 12

Allyl-(5R,6S,8R,2'S)-2-(2'-Allyloxycarbonylamino-2'-carboxyethylthio allyl ester)-6-(1-trichloroethoxycarbonyloxyethyl)-2-penem-3-carboxylate A. (3S,4R,5R,2'S)-3-(1-trichloroethyoxycarbonyloxyethyl)-4-[(2'-allyloxycarbonylamino-2'-carboxyethyl thio alkyl ester)carbonothioyl thio]-azetidin-2 one A solution of bis-(N-allyloxycarbonyl)-D-cysteine bis-allyl ester (14.76 g) in methanol (150 ml) containing zinc dust (15 g) is cooled to 0° C. and stirred while adding concentrated hydrochloric acid (10.4 ml) at a rate to maintain the temperature 0°-6° C. Following the addition of the acid, the mixture is stirred for an additional 2 minutes, poured on ice/water (200 ml), filtered and the organic layer of the filtrate is washed with water, dried over sodium sulfate and evaporated to dryness. The resulting oil is dissolved in ethanol (140 ml), treated with 1N sodium hydroxide (60–5 ml) followed by carbon disulfide (30 ml) and the resulting yellow solution is added dropwise with stirring to a solution of (3S,4R,5R)-3-(trichloroethoxycarbonyloxyethyl)-4-acetoxyazetidinone (19 g) in ethanol (100 ml) at −15° C. so that at the end of addition, the reaction mixture temperature is about 1° C. After about 45 minutes at this temperature and when thin layer chromatography indicates disappearance of starting material, the reaction is worked-up by pouring in ice/water (200 ml), extraction with ethylacetate (400 ml), washing the extract with brine, drying and evaporating. The resulting viscous yellow liquid is chromatographed on silica gel (500 g). Elution with 20% ethylacetatehexane afforded the title compound as an orange yellow glass IR: 5.6, 5.7, 5.8 u. $[\alpha]_D + 139°$ (chloroform); NMR ($C_DCl_3$): 1.5 (d,3H, J=6 cps); 3.42 (dd,1H, J=2;7 cps); 5.65 (d,1H, J=2 cps).

B. Allyl-(5R,6S,8R,2'S)-2-(2-(2'-allyloxycarbonyonylamino-2'-carboxyethyl thio allyl ester)-6-(1-trichloroethoxycarbonyloxyethyl)-2-penem-3-carboxylate A solution of (3S,4R,5R,2'S)-3-(1-trichloroethoxycarbonyloxyethyl)-4-[(2'-allyloxycarbonylamino-2'-carboxyethyl thio allyl ester)carbonothioyl thio]-azetidin-2-one (24.7 g) in methylene chloride (200 ml) containing calcium carbonate (25 g) is cooled to 5° C. and treated with a solution of allyloxalyl chloride (7.29 g) in methylene chloride (30 ml). The reaction mixure is stirred well while adding di-isopropyl ethylamine (8.42 ml) in methylene chloride (30 ml) at a rate to maintain the reaction temperature below 7° C. The mixture is stirred for an additional 10 minutes, and then worked-up by adding ice/water (100 ml) with vigorous stirring. The mixture is filtered and the organic layer of the filtrate is washed with ice/water (100 ml), dried in icebath with sodium sulfate and diluted to 1500 ml with ethanol free chloroform into a 21 3-neck flask. The diluted solution is refluxed while adding a solution of triethyl phosphite (16.7 ml) in chloroform (50 ml) during 3½ hours using a syringe pump. The reaction mixture is refluxed under nitrogen overnight and then evaporated under reduced pressure. The residual oil is chromatographed on silica gel (250 g). Elution with 20% ETOAC/hexane affords the title compound (21.2 g) as a colorless oil.

$[\alpha]_D + 111.6°$ (chloroform) 1R: (nujol) 5.58, 5.70, 5.80 u. NMR ($C_DCl_3$): 1.55 (d,3H, J=7 cps); 3.45 (d,2H, J=5 cps); 3.90 (dd,1H, J=2 cps); 5.65 (d,1H, J=2 cps).

What is claimed is:

1. A compound of the formula

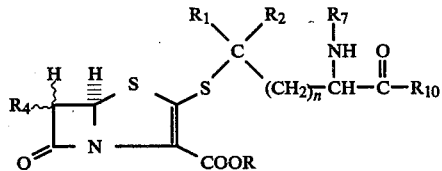

wherein n is 0 to 4;

R is hydrogen; an alkali metal cation; a quaternary ammonium cation or a metabolisable ester group;

$R_1$ and $R_2$ are independently hydrogen or lower alkyl;

$R_4$ is hydrogen, lower alkyl or a group of the formula

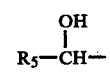

wherein:

$R_5$ is hydrogen; lower alkyl; phenyl; phenyl substituted by from 1 to 3 substituents independently selected from halogen, lower alkyl or lower alkoxy; lower alkyl substituted by phenyl or by phenyl substituted by from 1 to 3 substituents independently selected from halogen, lower alkyl or lower alkoxy; pyridyl; furanyl; thienyl; alkyl-substituted pyridyl, furanyl or thienyl; lower alkyl substituted by pyridyl, furanyl or thienyl; or lower alkyl substituted by lower alkyl-substituted pyridyl, furanyl or thienyl;

$R_{10}$ is amino, loweralkylamino, an α-amino acid residue bonded through the α-nitrogen atom or $OR_6$;

$R_6$ is hydrogen; lower alkyl; phenyl; phenyl substituted by from 1 to 3 substituents independently selected from halogen, lower alkyl or lower alkoxy; lower alkyl substituted by phenyl or by phenyl substituted by from 1 to 3 substituents independently selected from halogen, lower alkyl or lower alkoxy groups; an alkali metal cation; a quaternary ammonium cation; or a metabolisable ester group; R₇ is hydrogen; lower alkyl; phenyl; phenyl substituted by from 1 to 3 substituents independently selected from halogen, lower alkyl, or lower alkoxy; lower alkyl substituted by phenyl or by phenyl substituted by from 1 to 3 substituents independently selected from halogen, lower alkyl or lower alkoxy; phenylsulfonyl; phenylsulfonyl substituted by from 1 to 3 substituents independently selected from halogen, lower alkyl or lower alkoxy; methyl acetoacetyl; dihydroresorcinyl; dimedonyl; acetyl acetyl; a group

wherein R' is phenyl or phenyl substituted by 1 to 3 lower alkyl, lower alkoxy or halogen groups, and R" is hydrogen, lower alkyl or lower alkyl substituted by one or two phenyl or substituted phenyl groups, wherein the substituents on the phenyl are 1 to 3 halogen, lower alkyl or lower alkoxy groups; an amidine or guanidine group; or an acyl group of the formula

wherein:
R₈ is lower alkyl; lower alkoxy; phenoxy or substituted phenoxy; lower alkyl substituted by phenyl or by substituted phenyl; pyridyl; furanyl; thienyl; substituted pyridyl, furanyl or thienyl; lower alkyl substituted by pyridyl, furanyl or thienyl; lower alkyl substituted by substituted pyridyl, furanyl or thienyl; alkenyl or alkynyl of 2 to 6 carbon atoms; cycloalkyl of 4 to 6 carbon atoms; wherein the substituents are selected from 1 to 3 hydroxy, thio, alkylthio, lower alkyl, lower alkoxy, halogen, cyano, carboxy, nitro, amino, amino lower alkyl or halo-lower alkyl groups.

2. A compound according to claim 1 wherein R₄ is a group of the formula

3. A compound according to claim 2 wherein R₅ is methyl.

4. A compound according to claim 1 wherein R₁₀ is —OR₆ and R₄ is

5. A compound according to claim 4 wherein the stereochemistry is 5R,6S,8R.

6. A compound according to claim 5 wherein the stereochemistry at the amino acid carbon is R or S.

7. The compound according to claim 6 which is (5R,6S,8R, 2'S)-2-[(2'-amino-2'-carboxyethyl)thio]-6-(1-hydroxyethyl)-2-penem-3-carboxylic acid, sodium salt.

8. A pharmaceutical composition comprising an antibacterially effective amount of a compound of claim 1 together with a non-toxic pharmaceutically acceptable carrier.

9. A composition according to claim 8 wherein the compound is (5R,6S,8R,2'S)-2-[(2'-amino-2'-carboxyethyl)thio]-6-(1-hydroxyethyl)-2-penem-3-carboxylic acid, sodium salt.

10. A method of eliciting an antibacterial response in a warm-blooded animal having a susceptible bacterial infection which comprises administering to said animal a non-toxic, antibacterially effective amount of a compound of claim 1.

11. A method according to claim 10 wherein the compound administered is (5R,6S,8R,2'S)-2-[(2'-amino-2'-carboxyethyl)thio]-6-(1-hydroxyethyl)-2-penem-3-carboxylic acid, sodium salt.

12. A compound according to claim 5 wherein R is sodium or potassium.

13. A compound according to claim 6 which is (5R,6S,8R,2'S)-2-[(2'-amino-2'-carboxyethyl)thio]-6-(1-hydroxyethyl)-2-penem-3-carboxylic acid, pyridinium salt.

* * * * *